United States Patent [19]

Kroll

[11] Patent Number: 5,431,687
[45] Date of Patent: Jul. 11, 1995

[54] IMPEDANCE TIMED DEFIBRILLATION SYSTEM

[75] Inventor: Mark W. Kroll, Minnetonka, Minn.

[73] Assignee: Angeion Corporation, Minneapolis, Minn.

[21] Appl. No.: 44,462

[22] Filed: Apr. 9, 1993

[51] Int. Cl.$^6$ .............................................. A61N 1/39
[52] U.S. Cl. ...................................................... 607/8
[58] Field of Search ........................ 607/5, 8, 124, 142

[56] References Cited

U.S. PATENT DOCUMENTS

| | | | |
|---|---|---|---|
| 3,815,611 | 1/1974 | Denniston, III | 607/8 |
| 4,328,808 | 5/1982 | Charbonnier et al. | 128/419 |
| 4,574,810 | 3/1986 | Lerman | 607/8 |
| 4,840,177 | 6/1989 | Charbonnier et al. | 128/419 |
| 4,870,341 | 9/1989 | Pihl et al. | 324/57 |
| 5,111,813 | 5/1992 | Charbonnier et al. | 128/419 |
| 5,224,475 | 7/1993 | Berg et al. | 607/8 |

OTHER PUBLICATIONS

"Can Changes in Transcardiac Impedance Appropriately Detect Ventricular Fibrillation?" PACE, vol. 14, Feb. 1991, Part II.

Primary Examiner—Kyle L. Howell
Assistant Examiner—Marianne Parker
Attorney, Agent, or Firm—Joel D. Skinner

[57] ABSTRACT

An implantable cardiac defibrillator system, comprising:

a) a charge storage element, b) a switching element connected to the charge storage element, c) a processor capable of detecting a defibrillation event in a patient, d) patient connection electrodes connected to the switching element and to the processor, e) a cardiac impedance monitoring section connected to the patient connection electrodes, and f) a charge storage element discharge section communicatively connected to the switching element.

11 Claims, 3 Drawing Sheets

IMPEDANCE TIMED DEFIBRILLATION SYSTEM

BACKGROUND OF THE INVENTION

This invention relates to electromedical apparatus and methods and particularly to electronic circuitry and methods for use in a cardiac defibrillator. More particularly, this invention relates to a method of detecting varying impedance in a cardiac cycle and delivering a defibrillating shock at a predetermined period in the cycle. The impedance timed defibrillation method of the invention is useful for determining the optimum time to deliver a defibrillating shock to a patient, particularly one having an implanted cardioverter/defibrillator, to derive maximum efficiency therefrom.

The implantable defibrillator is a well recognized and important tool for resuscitating cardiac arrest patients. Defibrillation of the human heart is accomplished by applying an electrical waveform to the cardiac muscle with appropriate electrodes, causing the cessation of rapid uncoordinated contractions of the heart (fibrillation) and restoration of normal beating of the heart.

In the past, various devices and methods have been used and proposed to defibrillate the human heart. However, these devices and methods have significant limitations and shortcomings, including the inability to deliver a defibrillation shock having maximum efficiency. Specifically, no device or method is known to base the delivery of a defibrillation shock on the impedance of the cardiac region of a human patient, despite the fact that the relationship of defibrillation shock efficiency to impedance is relatively well known. This invention is based, in part, on the recognition that the impedance of the pre-cordial region of a human patient constantly changes due to breathing and cardiac function. The term cardiac impedance as used herein refers to impedance due to such breathing and cardiac function as well as to other anatomical and physiological factors.

Despite the need in the art for a device and method which overcomes the limitations and problems of the prior art, none insofar as is known has been proposed or developed. Accordingly, it an object of the present invention to provide a device and method which overcome the limitations and shortcomings of the prior art. It is a further object of this invention to provide an improved defibrillation method and device which are reliable and effective at defibrillating a human heart, and which derive maximum efficiency from a defibrillation shock. A particular object of the present invention is to provide a method and device which deliver a defibrillation shock at a period in the cardiac cycle when cardiac impedance is at a low point.

SUMMARY OF THE INVENTION

The present invention provides an implantable cardiac defibrillator system, comprising:
a) a charge storage element,
b) a switching element connected to the charge storage element,
c) a processor capable of detecting a defibrillation event in a patient,
d) patient connection apparatus connected to the switching element and to said processor,
e) a cardiac impedance monitoring section connected to the patient connection apparatus, and
f) a charge storage element discharge section communicatively connected to the switching element.

A preferred embodiment of the invention provides an implantable cardioverter/defibrillator system which is capable of timing the delivery of a defibrillation shock based on cardiac impedance information, comprising:
a) a charge storage element,
b) a switching element connected to the charge storage element,
c) a processor capable of detecting a defibrillation event in a patient,
d) at least two patient connection electrodes, connected to the switching element and to the processor,
e) means to monitor cardiac impedance, connected to the patient connection electrodes, and
f) means to discharge the charge storage element, the discharge means being communicatively connected to the switching element, whereby the defibrillation detection element detects a defibrillation event in a patient, the charge storage element is charge to a predetermined degree and simultaneously an impedance signal is derived via the impedance monitoring means, and charge is delivered from the charge storage element to the patient via the switching means and the patient connection electrodes at a predetermined time as determined by the discharge means.

These and other benefits of this invention will become clear from the following description by reference to the drawings.

DESCRIPTION OF THE PREFERRED EMBODIMENT

Figure 1:
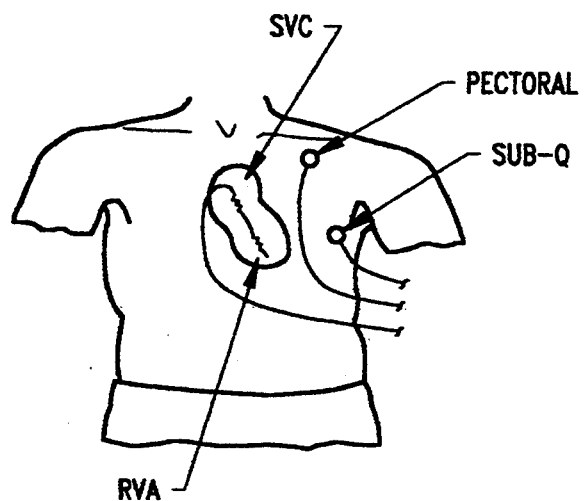
FIG. 1 is a representation of the human cardiac region showing common connections of defibrillator electrodes to the heart and chest region of a patient.

FIG. 1 shows a patient, his heart, and simplified electrodes attached in and/or around the heart. In a modern implanted cardioverter/defibrillator (ICD), there are typically 2, 3 or 4 electrodes, for example RVA, SVC, pectoral and Sub-Q. Impedance may be measured between any two electrodes or between various combinations of the electrodes. For example, measurement between RVA and SVC would primarily detect a cardiac cycle. As is known, one electrode may be a catheter indwelling in the heart and the other electrode may be a subcutaneous patch disposed outside the heart or heart region. Various electrode apparatus are known, as are methods of deploying them, for defibrillation purposes. For purposes of the present invention, at least two electrodes communicatively connected to heart are required.

Figure 2:
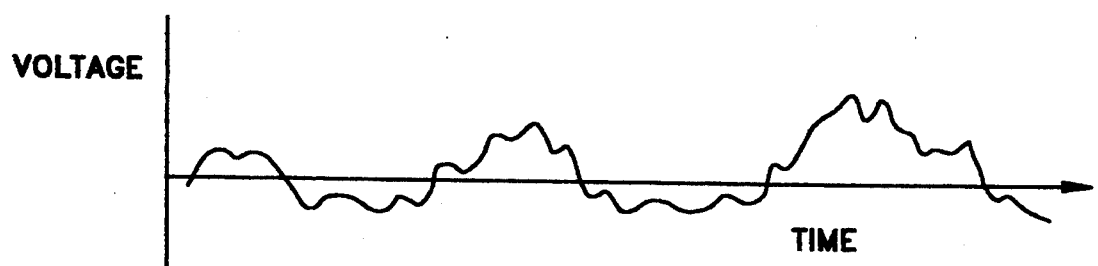
FIG. 2 shows a graph of an idealized voltage signal from common defibrillator electrodes, with respect to time.

FIG. 2 shows a graph of an idealized cardiac voltage signal as detected by the defibrillation and/or sensing electrodes. The voltage signal from the electrodes looks nearly random. As shown, cardiac signal voltage moves up and down with time.

Figure 4:
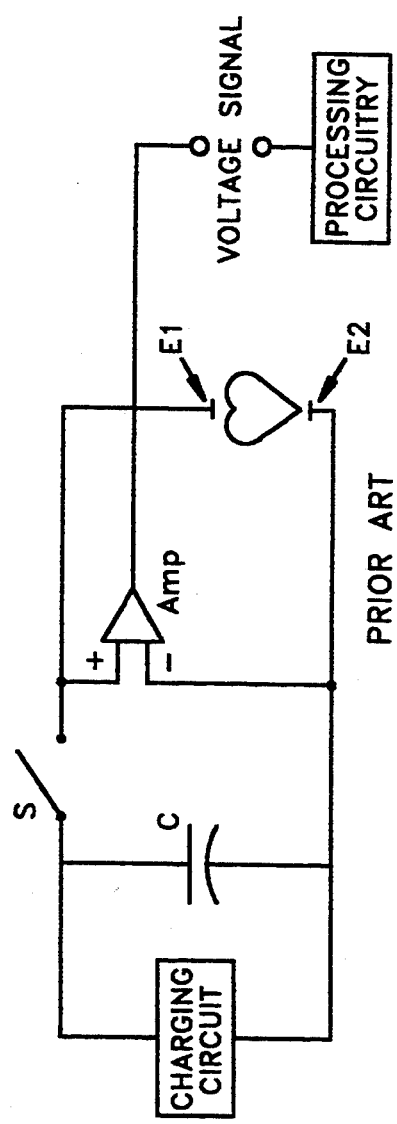
FIG. 4 is a schematic circuit diagram of a generalized prior art defibrillator apparatus.

Circuitry for a conventional device is shown in simplified form in FIG. 4. The voltage signal detected across electrodes E1 and E2 is amplified and produces a voltage signal similar to that shown in FIG. 2. In the alternative, the voltage signal may be taken from a separate set of designated "sensing" leads (not shown). When fibrillation is confirmed by an analysis of the voltage signal, a capacitor C is charged up to a very high voltage via a charge circuit, for example a battery and voltage inverter An electronic switch S is then turned "on" which delivers the charge in capacitor C to the heart. A popular alternative to this is to deliver the charge from capacitor C in a current flow of one direction to the heart for a predetermined time period followed by a reversal of current flow for a second time period. This is referred to as a "biphasic" defibrillation waveform. The circuitry shown in FIG. 4, however, generates a "monophasic" waveform. The impedance timing method of the present invention can be conducted with either type of basic waveform.

For a fixed pulse width, a given level of average current is required to defibrillate the heart. In accordance with Ohm's Law, the higher the impedance between electrodes E1 and E2, the higher the voltage that is required to provide this defibrillating current. Ohm's Law is given as:

Voltage = Current × Impedance.

The higher voltage requirement for a higher impedance directly translates into a larger size requirement for the capacitor C. This is undesirable since large implantable defibrillators present obvious difficulties for patients.

Another more subtle disadvantage exists in having a high impedance between electrodes E1 and E2. The amount of time taken to drain a capacitor C is proportional to the capacitance value of the capacitor C and the resistance that is the drain. Algebraically, this is given by:

Time Constant = Capacitance × Resistance

, where the Time Constant is the amount of time taken to deliver 63% of the charge from the capacitor C. With a high resistance, the capacitor C1 takes a longer time to deliver the charge. This can result in a large pulse width which is not frequency matched to the Time Constant of the heart. The Time Constant of the heart, known as the "chronaxie" time, is the width of a pulse that will defibrillate with minimum energy. Capacitors in present use in ICDs have values between 120–180 uF. For 50 Ohm impedances, their Time Constants vary between 6–9 ms. All of these Time Constants are greater than that of the heart and thus any increase in resistance, which will generate even wider pulses, will only decrease defibrillation efficiency.

Figure 3:
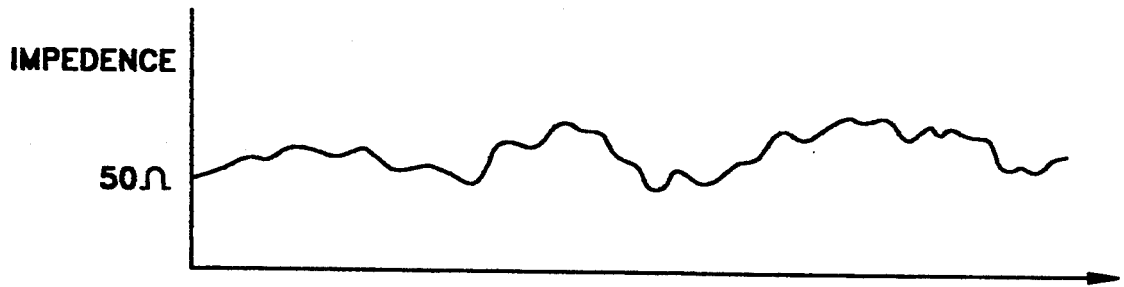
FIG. 3 shows a graph of an idealized impedance signal from a human heart with the same approximate time scale.

Thus, for the two reasons listed above, it is critical that impedance be as low as possible during a defibrillation shock. What is not generally appreciated is that the impedance of the heart varies throughout its fibrillation cycle and normal rhythm. The impedance to electrodes disposed at Sub-Q, for example, also changes with respect to respiration. This change in impedance is shown in FIG. 3, which shows a graph of an idealized impedance signal from a human heart as a function of time. The system of this invention detects this change and delivers the defibrillation shock during a period of low impedance.

Figure 5:
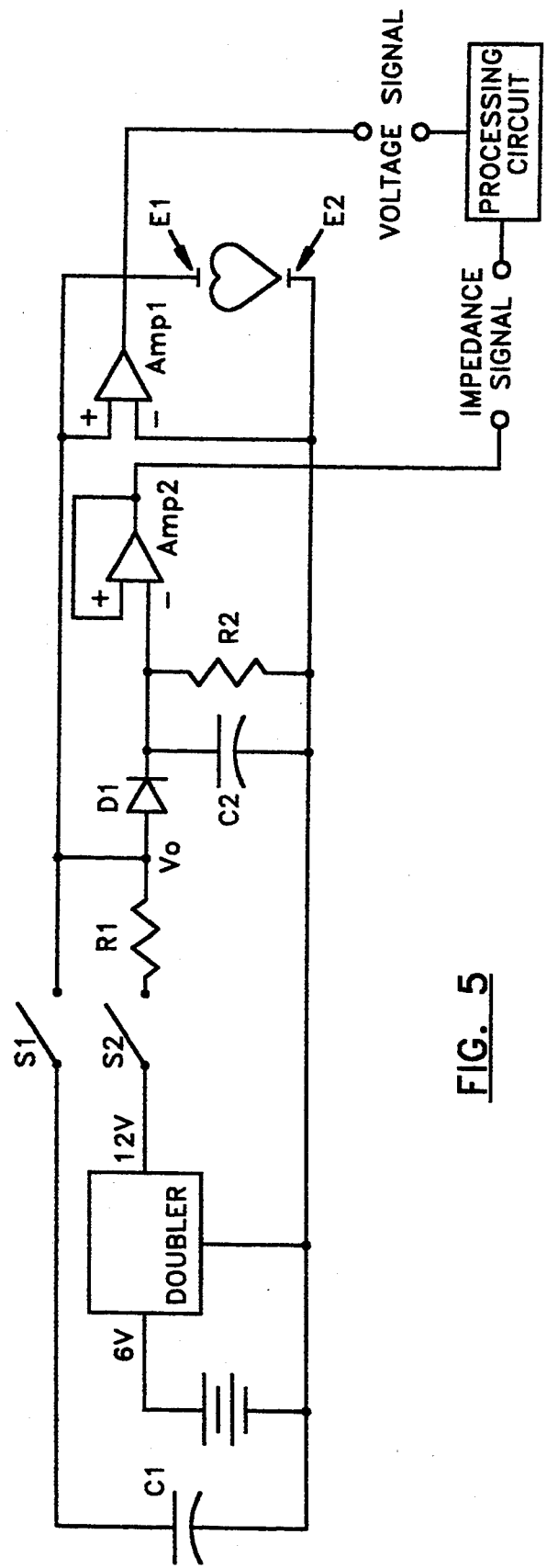
FIG. 5 is a schematic circuit diagram of the impedance timed defibrillation system of the present invention.

FIG. 5 shows a circuit for detecting bio-electric impedance and for timing the delivery of a defibrillation shock to a patient based on such detection. Capacitor C1 is chargeable to a high voltage and switch S1 is utilized to deliver capacitor C1 charge to the heart via electrodes E1 and E2. The capacitor must be capable of discharging an amount of energy on the order of 6–10 joules. Various types of switches are useable, but semiconductor switches such as transistors, thyristors and triacs are preferred. Amplifier Amp 1 is for detecting the voltage signal and delivering the signal to processing circuitry, to detect cardiac defibrillation. Ancillary circuitry such as high voltage protection circuits (not shown), known in the art, may be connected to this circuit.

Figure 6:
FIG. 6 shows a graph of representative impedance testing pulses from the system of this invention.

Six volts are shown being derived from the existing defibrillation batteries. The six volt level is processed by a doubler circuit to generate a 12 volt level. The voltage multiplication is helpful since the inter-electrode impedance is highly non-linear at lower voltages. For example, several volts are required at each electrode to merely turn "on" the electrode strongly. When fibrillation has been detected, switch S2 is pulsed "on" for short periods of time such as 3 ms. pulse widths or shorter that correspond with the shortest pulses expected from the defibrillation capacitor C1. An exemplary 12 volt pulse signal generated at switch S2 is shown in FIG. 6.

Figure 7:
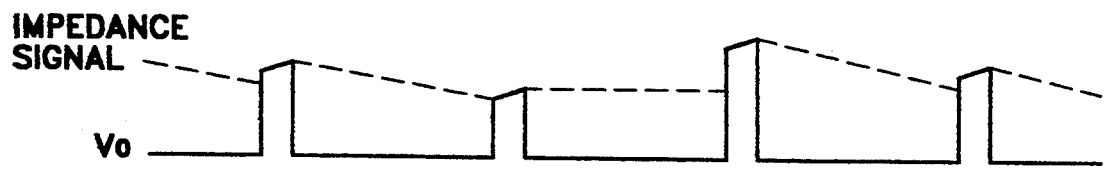
FIG. 7 shows a graph of a representative impedance signal as detected by the circuitry of this invention.

Resistor R1 forms a voltage divider in conjunction with the resistance of the heart. The voltage at the right of resistor R1 (Vo) will be lower if the impedance of the heart is lower and will generally track the impedance of the heart during the pulse generated by switch S2. An exemplary voltage signal (Vo) generated is shown in FIG. 7. That voltage (Vo) is then allowed to charge capacitor C2, in a one-way fashion because of diode D1, to form a longer lasting signal representing the impedance. Resistor R2 serves to slowly discharge capacitor C2 so that the peaks of Vo are not held infinitely long. The signal on capacitor C2 is then amplified by amplifier Amp 2 which then delivers an impedance signal to processing circuitry. This impedance signal is shown as the dashed line in FIG. 7, where Vo was the solid line. FIG. 7 is on an amplified time scale compared to the tracings of FIG. 2 and FIG. 3. The curves in FIGS. 6 and 7 constitute a fraction of a second, for example approximately 0.1 s. The curves in FIGS. 2 and 3 consist of 1.0 s or more of tracings.

The expected behavior of the circuit shown in FIG. 5 is as follows. Fibrillation is detected in the processing circuitry by a common technique such as the analysis of the voltage on the electrodes E1 and E2. The capacitor C1 is charged up to it's defibrillation voltage. During the several seconds that the capacitor C1 is being charged up, the impedance signal will be derived through the operation of switch S2 and processing circuitry as previously discussed. The processing circuitry analyzes the range of impedance detected. For illustrative purposes, the range of impedances is between 43–51 Ohms. After the capacitor C1 is fully charged, there may be an optional reconfirmation of fibrillation (in non-committed systems for example), before the charge is delivered in the heart.

Subsequent to the switch S2 pulsing, the processing circuitry monitors the impedance signal and waits for the impedance to come within a predetermined tolerance of the lowest impedance. For example, the processing circuitry determines the point at which electrode E1 and E2 impedance comes within 1 Ohm of the low value. In the instant example, at the time that this 44 Ohm impedance is detected, the shock is delivered by closing switch S1.

Because of the improved current flow through this lower impedance, there is an increased probability of successful defibrillation. In addition, the pulse width may be narrowed for higher efficiency.

As many changes are possible to the embodiments of this invention utilizing the teachings thereof, the descriptions above, and the accompanying drawings should be interpreted in the illustrative and not the limited sense.

That which is claimed is:

1. A defibrillator system of the type having a battery, a charge storage element, a switching element, a fibrillation detection element, and means to connect the switching element and the fibrillation detection element to a patient, the improvement which comprises means to monitor cardiac impedance and means to discharge the charge storage element at a predetermined time, said means to discharge being connected to the switching element and to said means to monitor cardiac impedance, whereby discharge of a defibrillation shock is based on monitored cardiac impedance.

2. The system of claim 1, wherein said means to monitor cardiac impedance comprises means to generate pulses of a predetermined voltage level and time period, a voltage divider connected to said pulse generation means and to said patient connection means, a capacitor connected to said voltage divider, and a processor connected to said capacitor.

3. The system of claim 2, wherein said pulse generation means comprises a a doubler circuit connected to the battery, and means to generate pulses from said from said doubler circuit.

4. The system of claim 3, wherein said pulse generation means generates 12 volt level pulses of a width which are less than or equal to the pulses generated by the charge storage element via the switching element.

5. The system of claim 4, wherein said voltage divider comprises a resistor connected to said pulse generation means, to the switching element and to the patient connection means.

6. The system of claim 5, wherein said capacitor is connected to said resistor through a diode, whereby said capacitor charges in a one-way mode to generate an impedance signal which is a function of patient cardiac impedance and which is transmitted to said processing means, and further wherein a second resistor is connected to said capacitor, whereby said impedance signal has peak amplitudes which are limited with respect to time.

7. The system of claim 6, further comprising an amplifier connected to said capacitor and to said processor means.

8. The system of claim 2, wherein said discharge means comprises said processor connected to the switching element.

9. The system of claim 1, wherein said fibrillation detection element detects a fibrillation event in a patient, the charge storage element is charged to a predetermined degree and simultaneously an impedance signal is derived via said impedance monitoring means, and charge is delivered from said charge storage element to the patient via the switching element and the patient connection means at a predetermined time as determined by said discharge means.

10. A cardiac defibrillator system, comprising:
 (a) a battery,
 (b) a charge storage element connected to said battery,
 (c) a switching element connected to said charge storage element,
 (d) means for detecting a fibrillation event in a patient,
 (e) at least two patient connection electrodes connected to said switching element and to said charge storage element, said electrodes further being adapted for connection to a cardiac region of the patient to receive and discharge electrical energy thereat,
 (f) means to monitor cardiac impedance and to determine a predetermined level of cardiac impedance, and
 (g) means to discharge said charge storage element, said discharge means being communicatively connected to said switching element, said means to discharge delivering charge from said charge storage element at said predetermined level of cardiac impedance.

11. An implantable cardioverter/defibrillator system which times delivery of a defibrillation shock to a patient's heart, after detection of a fibrillation event, based on cardiac impedance information, comprising:
 (a) a battery,
 (b) a charge storage element connected to said battery,
 (c) a switching element connected to said charge storage element,
 (d) means for detecting a fibrillation event in a patient,
 (e) at least two patient connection electrodes connected to said switching element and to said charge storage element, said electrodes further being adapted for connection to a cardiac region of the patient to receive and discharge electrical energy thereat,
 (f) means to monitor cardiac impedance and to determine a predetermined period of low cardiac impedance, within 1 ohm of a lowest detected impedance, after detection of cardiac fibrillation, said means to monitor cardiac impedance comprising a pulse generator connected to said battery and generating 12 volt pulses of not greater than 3 milliseconds, a voltage divider connected to said pulse generator and to said patient connection electrodes, a capacitor connected to said voltage divider and an amplifier connected to said voltage divider,
 (g) means to discharge said charge storage element, said discharge means being communicatively connected to said switching element, whereby a fibrillation event is first detected in the patient, said charge storage element is charged to a predetermined degree and simultaneously a cardiac impedance signal is derived via said means to monitor cardiac impedance, said predetermined period of low cardiac impedance is detected, and charge is delivered from said charge storage element to the patient via the switching means and the patient connection electrodes.

* * * * *